United States Patent
Yu et al.

(10) Patent No.: US 11,058,624 B2
(45) Date of Patent: *Jul. 13, 2021

(54) HAIR CARE COMPOSITION COMPRISING CATIONIC POLYMERS AND ANIONIC PARTICULATES

(71) Applicant: The Procter & Gamble Company, Cincinnati, OH (US)

(72) Inventors: Kristine Suzanne So Yu, Singapore (SG); Mannie Lee Clapp, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/174,401

(22) Filed: Feb. 6, 2014

(65) Prior Publication Data
US 2015/0216786 A1    Aug. 6, 2015

(51) Int. Cl.
| | | |
|---|---|---|
| A61K 8/81 | (2006.01) | |
| A61K 8/34 | (2006.01) | |
| A61K 8/19 | (2006.01) | |
| A61K 8/49 | (2006.01) | |
| A61K 8/27 | (2006.01) | |
| A61Q 5/12 | (2006.01) | |
| A61Q 5/02 | (2006.01) | |
| A61K 8/42 | (2006.01) | |
| A61K 8/25 | (2006.01) | |
| A61K 8/41 | (2006.01) | |
| A61K 8/84 | (2006.01) | |
| A61K 8/02 | (2006.01) | |

(52) U.S. Cl.
CPC ............ *A61K 8/817* (2013.01); *A61K 8/0241* (2013.01); *A61K 8/19* (2013.01); *A61K 8/25* (2013.01); *A61K 8/27* (2013.01); *A61K 8/342* (2013.01); *A61K 8/416* (2013.01); *A61K 8/42* (2013.01); *A61K 8/4933* (2013.01); *A61K 8/84* (2013.01); *A61Q 5/12* (2013.01); *A61K 2800/30* (2013.01); *A61K 2800/412* (2013.01); *A61K 2800/5426* (2013.01); *A61K 2800/58* (2013.01)

(58) Field of Classification Search
None
See application file for complete search history.

(56) References Cited

U.S. PATENT DOCUMENTS

| | | | |
|---|---|---|---|
| 4,275,055 | A | 6/1981 | Nachtigal et al. |
| 4,557,928 | A | 12/1985 | Glover |
| 5,723,112 | A | 3/1998 | Bowser et al. |
| 6,908,912 | B2 | 6/2005 | Rioux et al. |
| 6,979,439 | B1 * | 12/2005 | Sakai et al. ................... 424/70.8 |
| 7,026,308 | B1 | 4/2006 | Gavin et al. |
| 7,037,513 | B1 | 5/2006 | Traynor et al. |
| 7,455,851 | B1 | 11/2008 | Nelson et al. |
| 7,674,785 | B2 | 3/2010 | Gavin et al. |
| 8,206,732 | B2 | 6/2012 | Nelson et al. |
| 8,273,332 | B2 | 9/2012 | Gross et al. |
| 8,796,252 | B2 | 8/2014 | Rioux et al. |
| 9,132,289 | B2 | 9/2015 | Kawai |
| 2004/0058855 | A1 | 3/2004 | Schwartz et al. |
| 2004/0191331 | A1 | 9/2004 | Schwartz et al. |
| 2004/0213751 | A1 * | 10/2004 | Schwartz et al. ............ 424/70.1 |
| 2007/0128147 | A1 | 6/2007 | Schwartz et al. |
| 2007/0248551 | A1 | 10/2007 | Lemoine |
| 2008/0206355 | A1 * | 8/2008 | Schwartz .............. A61K 8/4933 424/604 |
| 2010/0247472 | A1 | 9/2010 | Sau |
| 2010/0322885 | A1 | 12/2010 | Ueno |
| 2011/0294773 | A1 | 12/2011 | Ishikubo et al. |
| 2012/0058071 | A1 | 3/2012 | Gross et al. |
| 2012/0064137 | A1 | 3/2012 | Kawai |
| 2012/0088807 | A1 | 4/2012 | Krouse et al. |
| 2012/0251627 | A1 | 10/2012 | Nelson et al. |
| 2012/0316239 | A1 | 12/2012 | Okada et al. |
| 2013/0259817 | A1 | 10/2013 | Uehara et al. |
| 2013/0259820 | A1 | 10/2013 | Snyder et al. |
| 2013/0276808 | A1 * | 10/2013 | Molenda et al. .............. 132/202 |
| 2013/0280193 | A1 | 10/2013 | Carter et al. |
| 2014/0335040 | A1 | 11/2014 | Yu et al. |
| 2015/0165690 | A1 | 6/2015 | Tow |
| 2015/0216769 | A1 | 8/2015 | Takahashi |
| 2015/0216770 | A1 | 8/2015 | Takahashi et al. |
| 2015/0216774 | A1 | 8/2015 | Yu et al. |
| 2015/0216777 | A1 | 8/2015 | Takahashi |
| 2015/0216984 | A1 | 8/2015 | Yu |
| 2016/0235651 | A1 | 8/2016 | Decoster |
| 2016/0374431 | A1 | 12/2016 | Tow |
| 2017/0105917 | A1 | 4/2017 | Iwata |
| 2017/0105918 | A1 | 4/2017 | Iwata |
| 2017/0105919 | A1 | 4/2017 | Iwata |
| 2018/0200171 | A1 | 7/2018 | Iwata |
| 2020/0108003 | A1 | 4/2020 | Iwata |

FOREIGN PATENT DOCUMENTS

| | | |
|---|---|---|
| CN | 101112349 B | 5/2011 |
| DE | 102012203240 A1 | 3/2013 |

(Continued)

OTHER PUBLICATIONS

Fevola, Michael J. "Polyquaternium-6." Cosmetics and toiletries 126.3 (Mar. 2011) 150-154.*

(Continued)

*Primary Examiner* — Bethany P Barham
*Assistant Examiner* — Peter Anthopolos
(74) *Attorney, Agent, or Firm* — Linda M. Sivik

(57) ABSTRACT

Disclosed is a hair care composition comprising cationic polymers and anionic particulates. The composition of the present invention provides improved deposition of anionic particulates.

3 Claims, No Drawings

(56) References Cited

FOREIGN PATENT DOCUMENTS

| | | |
|---|---|---|
| EP | 0060611 A2 | 9/1982 |
| EP | 0074819 | 3/1983 |
| EP | 1527768 A1 | 5/2005 |
| EP | 1504744 B1 | 7/2010 |
| JP | 58065210 | 4/1983 |
| JP | 2007277227 A | 10/2007 |
| JP | 4955959 B2 | 6/2012 |
| KR | 2001-0045153 | 11/1999 |
| WO | 9913844 A1 | 3/1999 |
| WO | WO2001/35912 | 5/2001 |
| WO | WO03/088965 | 3/2004 |
| WO | WO2004/082649 | 9/2004 |
| WO | WO2007001844 A1 | 1/2007 |
| WO | WO2009016555 A1 | 2/2009 |
| WO | WO2011009710 A1 | 1/2011 |
| WO | WO2012119825 A2 | 9/2012 |
| WO | WO2013072163 A1 | 5/2013 |
| WO | WO2014124066 A1 | 8/2014 |
| WO | WO2014124070 A1 | 8/2014 |
| WO | WO2015133382 A1 | 9/2015 |

OTHER PUBLICATIONS

U.S. Appl. No. 14/174,317, filed Feb. 6, 2014, Kenji Takahashi.
U.S. Appl. No. 14/174,362, filed Feb. 6, 2014, Kenji Takahashi.
U.S. Appl. No. 14/174,377, filed Feb. 6, 2014, Kenji Takahashi.
U.S. Appl. No. 14/174,389, filed Feb. 6, 2014, Kenji Takahashi.
U.S. Appl. No. 14/174,415, filed Feb. 6, 2014, Kristine Suzanne So Yu.
U.S. Appl. No. 14/174,433, filed Feb. 6, 2014, Kristine Suzanne So Yu.
International Search Report; PCT/US2014/014973; dated Jun. 2, 2014.
Extra Fullness Dandruff Condition; Database GNPD Mintel Jul. 2004.
Lubrizol Advanced Materials, Inc., "Merquat 106 Polymer Technical Datasheet", Nov. 1, 2011.
PCT International Search Report and Written Opinion for PCT/US2014/014974 dated Jun. 2, 2014.
PCT International Search Report and Written Opinion for PCT/US2014/014975 dated Jun. 2, 2014.
PCT International Search Report and Written Opinion for PCT/US2014/014977 dated Jun. 2, 2014.
All final and non-final office actions for U.S. Appl. No. 15/293,709.
All final and non-final office actions for U.S. Appl. No. 15/293,731.
All final and non-final office actions for U.S. Appl. No. 15/293,747.
All final and non-final office actions for U.S. Appl. No. 15/921,247.
PCT International Search Report and Written Opinion for PCT/US2016/056930 dated Feb. 1, 2017.
PCT International Search Report and Written Opinion for PCT/US2016/056931 dated Feb. 1, 2017.
PCT International Search Report and Written Opinion for PCT/US2016/056932 dated Feb. 1, 2017.
GNPD Database—"2 in 1 Shampoo and Conditioner", Nov. 15, 2011.
GNPD database—"Anti Dandruff 2 in 1 Shampoo", Aug. 11, 2014.
GNPD Database—"Fortifying Anti-Dandruff Shampoo", Feb. 13, 2008.
PCT International Search Report and Written Opinion for PCT/US2019/054425 dated Dec. 4, 2019.

* cited by examiner

HAIR CARE COMPOSITION COMPRISING CATIONIC POLYMERS AND ANIONIC PARTICULATES

FIELD OF THE INVENTION

The present invention relates to a hair care composition comprising cationic polymers and anionic particulates. The composition of the present invention provides improved deposition of anionic particulates.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. Furthermore, a variety of approaches have been developed to provide other benefits in addition to such conditioning benefits.

Anionic particulates are sometimes incorporated into the above compositions to provide such other benefits. For example, P&G's WO03/088965 and WO2004/082649 disclose conditioner compositions containing $ZnCO_3$, which is believed to enhance antidandruff benefit from zinc pyrithione. For another example, come conditioning compositions contains silica.

There is a need for such compositions to provide improved deposition of such anionic particulates on hair and/or scalp.

None of the existing art provides all of the advantages and benefits of the present invention.

SUMMARY OF THE INVENTION

The present invention is directed to a hair care composition comprising by weight:
(a) from about 0.1% to about 10% of a cationic surfactant system;
(b) from about 0.1% to about 20% of a high melting point fatty compound;
(c) from about 0.01% to about 5% of an anionic particulate;
(d) from about 0.01% to about 5% of a cationic polymer; and
(e) an aqueous carrier, The composition of the present invention provides improved deposition of anionic particulates.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated.

Composition

The composition comprises a cationic surfactant system; a high melting point fatty compound; a cationic polymer; an anionic particulate; and an aqueous carrier.

These ingredients, as well as the gel matrix formed by some of these ingredients, are explained below in detail.

The composition of the present invention is, preferably, substantially free of anionic surfactants in view of avoiding undesirable interaction with cationic surfactants and/or in view of stability of the gel matrix. In the present invention, "the composition being substantially free of anionic surfactants" means that: the composition is free of anionic surfactants; or, if the composition contains anionic surfactants, the level of such anionic surfactants is very low. In the present invention, the total level of such anionic surfactants is, if included, 1% or less, preferably 0.5% or less, more preferably 0.1% or less, still more preferably 0% by weight of the composition.

Cationic Polymer

The composition of the present invention comprises a cationic polymer. The cationic polymer can be included in the composition at a level by weight of from about 0.01% to about 5%, preferably from about 0.05% to about 1%, more preferably from about 0.05% to about 0.3%, in view of providing improved deposition of anionic particulates through interaction with anionic particulates, while providing improved conditioning benefit It is preferred that the cationic polymer and anionic particulates and are included such that the weight ratio of the cationic polymer and anionic particulates is from about 1:1000 to about 1000:1, more preferably from about 1:500 to about 500:1, still more preferably from about 1:100 to about 100:1 in view of providing improved deposition of anionic particulates.

The cationic polymer useful herein is that having a cationic charge density of, preferably from about 3.5 meq/g, more preferably from about 4.5 meq/g, still more preferably from about 5.5 meq/g in view of providing improved deposition of metal pyrithione, and preferably to about 13.0 meq/g more preferably to about 10.0 meq/g, still more preferably to about 7.0 meq/g in view of providing improved deposition of anionic particulates.

The cationic polymer useful herein is that having a molecular weight of, preferably about 800 g/mol or more, more preferably 1,000 g/mol or more, still more preferably 1,200 g/mol or more in view of providing improved deposition of anionic particulates. The molecular weight is up to about 3,000,000 g/mol, preferably up to about 1,000,000 g/mol, more preferably to about 500,000 g/mol, still more preferably 100,000 g/mol, even more preferably 50,000 g/mol in view of providing better conditioning while providing improved deposition of anionic particulates.

Cationic polymers useful herein include, for example, are Polyquaternium-4, Polyquaternium-5, Polyquaternium-6, Polyquaternium-7, Polyquaternium-10, Polyquaternium-11, Polyquaternium-15, Polyquaternium-22, Polyquaternium-67, cationic guar polymers, Polyethyleneimines, and hexadimethrine chloride. Preferred are polyqueternium-6, Polyethyleneimines and hexadimethrine chloride, more preferred is polyquaternium-6.

Among a variety of cationic polymers, highly preferred is polyquaternium-6 polymer which include, for example, that having a tradename Merquat 100 available from Lubrizol, which has a cationic charge density of about 6.19 meq/g, molecular weight of about 150,000 g/mol, and that having a tradename Merquat 106 available from Lubrizol, which has a cationic charge density of about 6.19 meq/g, molecular weight of about 15,000 g/mol.

Anionic Particulate

The composition of the present invention comprises an anionic particulate. The anionic particulate can be used at levels by weight of the composition of preferably from about 0.05% to about 10%, more preferably from about 0.01% to about 5%, still more preferably from about 0.1% to about 3% in view of delivering the above benefits.

Preferably, such anionic particulates are those which remain mostly insoluble within formulated compositions. "Being insoluble within the formulated compositions" herein means that the material remains as solid particulates and do not dissolve in the formula D(90) is the particle size which corresponds to 90% of the amount of particles are below this size. The anionic particulates preferably have a particle size distribution wherein 90% of the particles are less than about 50 microns. In a further embodiment of the present invention, the particulate may have a particle size distribution wherein 90% of the particles are less than about 30 microns. In yet a further embodiment of the present invention, the particulate may have a particle size distribution wherein 90% of the particles are less than about 20 microns. Also, the anionic particulates preferably have a particle size distribution wherein 90% of the particles are 0.5 microns or more.

Anionic particulate useful herein can be, either particulates which naturally have anionic charge, or non-anionic particulates which is coated or premixed by anionic polymers, preferably, particulates which naturally have anionic charge.

Such "particulates which naturally have anionic charge" include, for example, silicas (or silicon dioxides), silicates, carbonates, and combinations thereof. Non-limiting examples of silicates are calcium silicate, amorphous silicas and non-limitng examples of carbonates include zinc hydroxyl carbonate, hydrozincite (zinc carbonate hydroxide), basic zinc carbonate, aurichalcite (zinc copper carbonate hydroxide), rosasite (copper zinc carbonate hydroxide). Non-limiting examples of some suitable silicates and carbonates for use herein are described in the 4th edition of Van Nostrand Reinhold's Encyclopedia of Chemistry, pp 155, 169, 556, and 849 (1984).

Among them, preferred are zinc hydroxyl carbonate, hydrozincite (zinc carbonate hydroxide), basic zinc carbonate, aurichalcite (zinc copper carbonate hydroxide), rosasite (copper zinc carbonate hydroxide) and combinations thereof. More preferred is hydrozincite (zinc carbonate hydroxide).

Such "non-anionic particulates which is coated or premixed by anionic polymers" include, for example, metal pyrithiones particles, pigment particles, starch and modified starch particles, silica particles, polyethylene (such as microthene) particles, polypropylene particles and polymeric microcapsules which are then coated or premixed by anionic polymers.

Among them, preferred are metal pyrithione coated or premixed by anionic polymers. Metal pyrithiones useful herein are heavy metal salts of 1-hydroxy-2-pyridinethione, the heavy metal salts being zinc, tin, cadmium, magnesium, aluminium, barium, bismuth, strontium, copper, and zirconium. Preferred are zinc and copper. More Preferred is zinc salt of 1-hydroxy-2-pyridinethione known in the art as zinc pyrithione, more preferably in a particle size of up to about 20 microns, still preferably from about 1 to about 10 microns.

It is preferred that the weight ratio of the anionic polymer to metal pyrithione, is from about 1:1 to about 1:100, more preferably from about 1:10 to about 1:50 still more preferably from about 1:20 to about 1:30, in view of improving suspension of metal pyrithiones, Anionic polymers useful herein are, for example, those having a molecular weight of preferably from about 100 g/mol to about 100,000 g/mol more preferably from about 1,000 g/mol to about 10,000 g/mol still more preferably from about 1,000 g/mol to about 5,000 g/mol in comparison to standards of sodium poly(styrenesulfonate) in view of having the ability to suspend solids and prevent their agglomeration, and those having a charge density of from about 1.0 meq/g to about 10 meq/g more preferably from about 2.0 meq/g to about 7 meq/g still more preferably from about 3.0 meq/g to about 5.0 meq/g in view of compatibility with cationic materials and stability of the formula.

Anionic polymers useful herein include, for example, sodium polynaphthalene sulfonate, Sodium Lignosulfonate, sodium carboxymethyl cellulose, Sodium salt of hydrophobically modified maleic anhydride copolymer, Sodium polyacrylate, sodium polymethacrylate, ammonium polyacrylate, ammonium polymethacrylate, Sodium salt of polymethacrylic acid, preferably sodium polynaphthalene sulfonate, and sodium carboxymethyl cellulose, and more preferably sodium polynaphthalene sulfonate, still more preferably sodium polynaphthalene sulfonate having a tradename Darvan1 Spray Dried, supplied from Vanderbilt Minerals having a molecular weight of about 3,000 g/mol in comparison to standards of sodium poly(styrenesulfonate) and a charge density of from about 3.5 to about 4.0 meq/g.

Cationic Surfactant System

The composition of the present invention comprises a cationic surfactant system. The cationic surfactant system can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt. More preferably, the cationic surfactant system is a mixture of mono-long alkyl quaternized ammonium salt and di-long alkyl quaternized ammonium salt.

The cationic surfactant system is included in the composition at a level by weight of from about 0.1% to about 10%, preferably from about 0.5% to about 8%, more preferably from about 0.8% to about 5%, still more preferably from about 1.0% to about 4%. Mono-long alkyl quaternized ammonium salt The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula

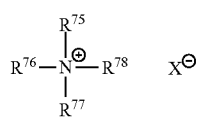

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as f-glutamic acid, lactic acid, hydrochloric acid, malic acid, succinic acid, acetic acid, fumaric acid, tartaric acid, citric acid, f-glutamic hydrochloride, maleic acid, and mixtures thereof; more preferably f-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

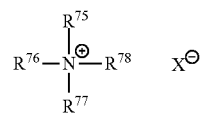

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

High Melting Point Fatty Compound

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

The high melting point fatty compound is included in the composition at a level of from about 0.1% to about 20%, preferably from about 1% to about 15%, more preferably from about 1.5% to about 8% by weight of the composition, in view of providing improved conditioning benefits such as slippery feel during the application to wet hair, softness and moisturized feel on dry hair.

Aqueous Carrier

The conditioning composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 95% water.

Gel Matrix

The composition of the present invention comprises a gel matrix. The gel matrix comprises a cationic surfactant, a high melting point fatty compound, and an aqueous carrier.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

Silicone Conditioning Agent

The compositions of the present invention may further contain a silicone conditioning agent. The silicone conditioning agent herein can be used at levels by weight of the composition of preferably from about 0.1% to about 20%, more preferably from about 0.5% to about 10%, still more preferably from about 1% to about 8%.

Preferably, the silicone compounds have an average particle size of from about 1microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):

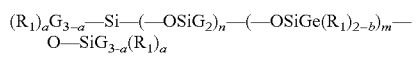

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3A^-$; —N($R_2$)$CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; A is a halide ion.

Highly preferred amino silicones are those corresponding to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Another highly preferred amino silicones are those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetra-acetate; and ultraviolet and infrared screening and absorbing agents such as octyl salicylate.

Product Forms

The conditioning compositions of the present invention can be in the form of rinse-off products or leave-on products, and can be formulated in a wide variety of product forms, including but not limited to creams, gels, emulsions, mousses and sprays.

The conditioning composition of the present invention is especially suitable for rinse-off hair conditioner. Such compositions are preferably used by following steps:
(i) after shampooing hair, applying to the hair an effective amount of the conditioning compositions for conditioning the hair; and
(ii) then rinsing the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

TABLE 1

| | Compositions | |
|---|---|---|
| Components | Ex. 1 | CEx. i |
| Polyquaternium-6 *1 | 0.075 | — |
| Polyquaternium-6 *2 | — | — |
| Zinc pyrithione *3 | 0.75 | 0.75 |

TABLE 1-continued

| Compositions | | |
|---|---|---|
| Components | Ex. 1 | CEx. i |
| Sodium polynaphthalene sulfonate *4 | 0.03 | 0.03 |
| Zinc carbonate *5 | 1.6 | 1.6 |
| Stearamidopropyldimethylamine | 2.0 | 2.0 |
| l-glutamic acid | 0.64 | 0.64 |
| Cetyl alcohol | 2.5 | 2.5 |
| Stearyl alcohol | 4.5 | 4.5 |
| Polydimethylsiloxane *6 | 4.2 | 4.2 |
| Preservatives | 0.9 | 0.9 |
| Perfume | 0.5 | 0.5 |
| Deionized Water | q.s. to 100% | |
| Method of preparation | I | |
| Deposition of Zinc pyrithione | SSS | C- |
| Deposition of Zinc carbonate | S | B |

TABLE 2

| | Compositions | | | | | | |
|---|---|---|---|---|---|---|---|
| Components | Ex. 2 | Ex. 3 | Ex. 4 | Ex. 5 | Ex. 6 | Ex. 7 | Ex. 8 |
| Polyquaternium-6 *1 | 0.075 | — | 0.075 | — | — | — | — |
| Polyquaternium-6 *2 | — | 0.075 | — | — | 0.075 | 0.075 | 0.050 |
| Polyquaternium-10 *7 | — | — | — | 0.075 | — | — | — |
| Zinc pyrithione *3 | 0.75 | 0.75 | 0.75 | 0.75 | 0.75 | 0.75 | 0.5 |
| Zinc carbonate *5 | 1.6 | 1.6 | 1.6 | 1.6 | 1.6 | 2.0 | — |
| Silica *8 | — | — | — | — | — | — | 1.0 |
| Behenyl trimethyl ammonium chloride | — | — | — | — | 2.5 | — | — |
| Behenyl trimethyl ammonium methosulfate | 2.6 | 2.6 | 2.0 | 2.6 | — | 2.5 | 2.5 |
| Dicetyl dimethyl ammonium chloride | — | — | — | — | — | 0.1 | — |
| Cetyl alcohol | 1.0 | 1.0 | 1.4 | 1.0 | 2.0 | 2.0 | 2.0 |
| Stearyl alcohol | 2.4 | 2.4 | 3.4 | 2.4 | 4.0 | 4.0 | 4.0 |
| Aminosilicone *9 | 0.5 | 0.5 | 0.5 | 0.5 | 0.5 | 0.5 | 0.5 |
| Preservatives | 0.9 | 0.9 | 0.9 | 0.9 | 0.9 | 0.9 | 0.9 |
| Perfume | 0.5 | 0.5 | 0.5 | 0.5 | 0.5 | 0.5 | 0.5 |
| Panthenol | — | — | — | — | — | 0.05 | — |
| Panthenyl ethyl ether | — | — | — | — | — | 0.03 | — |
| Deionized Water | q.s. to 100% | | | | | | |
| Method of preparation | I-mod | I-mod | II | I-mod | I | I | I |
| Deposition of Zinc carbonate | S | S | S | A | — | — | — |

Definitions of Components

*1 Polyquaternium-6: Poly(diallyldimethylammonium chloride) supplied with atradename Merquat 100 from Nalco, having a charge density of about 6.2 meq/g, and molecular weight of about 150,000 g/mol

*2 Polyquaternium-6:Poly(diallyldimethylammonium chloride) supplied with atradename Merquat 106 from Nalco having a charge density of about 6.2 meq/g, and molecular weight of about 15,000 g/mol

*3 Zinc pyrithione: having a particle size of from about 1 to about 10 microns

*4 Sodium polynaphthalene sulfonate having atradename Darvani Spray Dried, supplied from RT Vanderbilt having a molecular weight of about 3,000 g/mol in comparison to standards of sodium poly(styrenesulfonate) and a charge density of from about 3.5 to about 4.0 meq/g

*5 Zinc carbonate: having a particle size of from about 1 to about 10 microns

*6 Polydimethylsiloxane: having a viscosity of 10,000 cSt

*7 Polyquaternium-10: Quaternized hydroxyethylcellulose supplied with a tradename Ucare Polymer JR-400 from Dow Chemical

*8 Silica: having a particle size of 0.5 to 20 microns

*9 Aminosilicone: Terminal aminosilicone which is available from GE having a viscosity of about 10,000 mPa·s, and having following formula:

wherein G is methyl; a is an integer of 1; n is a number from 400 to about 600; $R_1$ is a monovalent radical conforming to the general formula $C_qH_{2q}L$, wherein q is an integer of 3 and L is —$NH_2$.

Method of Preparation

The conditioning compositions of "Ex. 1" through "Ex. 8" and "CEx. i" as shown above can be prepared by any conventional method well known in the art. They are suitably made by one of the following Methods I, I-mod, or II as shown above.

Method I

Cationic surfactants and high melting point fatty compounds are added to water with agitation, and heated to about 80° C. The mixture is cooled down to about 55° C. and gel matrix is formed. Silicones, preservatives, zinc carbonates are added to the gel matrix with agitation. Separately, zinc pyrithione premixed in Sodium polynaphthalene sulfonate in water solution if Sodium polynaphthalene sulfonate included. Then zinc pyrithione with or without Sodium polynaphthalene sulfonate, and if included, polymers are added with agitation at about 45° C. Then, if included, other components such as perfumes are added with agitation. Then the composition is cooled down to room temperature.

Method I-Mod

Cationic surfactants and high melting point fatty compounds are added to water with agitation, and heated to about 80° C. The mixture is cooled down to about 55° C. and gel matrix is formed. Silicones, perfumes, preservatives, zinc carbonates are added to the gel matrix with agitation. Then, zinc pyrithione, and if included, polymers are added with agitation at about 30° C. Then, if included, other components are added with agitation.

Method II

Cationic surfactants and high melting point fatty compounds are mixed and heated to from about 66° C. to about 85° C. to form an oil phase. Separately, water is heated to from about 20° C. to about 48° C. to form an aqueous phase. In Becomix® direct injection rotor-stator homogenizer, the oil phase is injected and it takes 0.2 second or less for the oils phase to reach to a high shear field having an energy density of from $1.0 \times 10^5$ J/m³ to $1.0 \times 10^7$ J/m³ where the aqueous phase is already present. A gel matrix is formed at a temperature of above 50° C. to about 60° C. Silicones, preservatives, zinc carbonates are added to the gel matrix with agitation. Then, zinc pyrithione, and if included, polymers are added with agitation at about 32° C. Then, if included, other components such as perfumes are added with agitation. Then the composition is cooled down to room temperature.

Properties and Benefits

For some of the compositions, some benefits are evaluated by the following methods. Results of the evaluation are shown above.

Examples 1 through 8 are hair conditioning compositions of the present invention which are particularly useful for rinse-off use. The embodiments disclosed and represented by the previous "Ex. 1" through "Ex. 8" have many advantages. For example, they provide improved deposition of anionic particulates such as zinc carbonate, silica, and/or metal pyrithiones premixed in Sodium polynaphthalene sulfonate.

Such advantages can be understood by the comparison between the examples of the present invention and comparative example "CEx. i".

For example, comparison between Ex. 1 and CEx. i in Table 1 shows that the composition of Ex. 1 provides improved deposition of zinc carbonate, and also zinc pyrithione premixed in Sodium polynaphthalene sulfonate on scalp, compared to the composition of CEx. i which is almost identical to Ex. 1 except for the absence of polyquaternium-6. Also, the compositions of Ex. 2-5 also provide improved deposition of zinc carbonate on scalp.

Deposition Test

The on-scalp deposition of the anti-dandruff active is measured by having the hair of individuals. First, a shampoo containing 1% zinc pyrithione and 1.6% of zinc carbonate is applied to the hair, and washed away. Then, one of the compositions of the above examples is applied, and rinsed off. The hair is parted on an area of the scalp to allow an open-ended glass cylinder to be held on the surface while an aliquot of an extraction solution is added and agitated prior to recovery and analytical determination of zinc pyrithione and zinc carbonate content by conventional methodology, such as HPLC.

Evaluation

SSS: Above 200% (Excluding 200%) to 350% increased deposition, compared to Control SS: Above 100% (Excluding 100%) to 200% increased deposition, compared to Control S: Above 50% (Excluding 50%) to 100% increased deposition, compared to Control.

A: Above 25% (Excluding 25%) to 50% increased deposition, compared to Control.

B: Above 10% (Excluding 10%) to 25% increased deposition, compared to Control.

C+: Up to 10% increased deposition, compared to Control.

C: Control (which is zinc pyrithione deposition amount or zinc carbonate deposition amount, after shampooing.)

C−: Up to 10% decreased deposition, compared to Control.

D: Above 10% decreased deposition, compared to Control

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the same term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition comprising by weight:
   (a) from about 0.1% to about 10% of a cationic surfactant system;
   (b) from about 0.1% to about 20% of a high melting point fatty compound having a melting point of 25° C. or higher and is selected from the group consisting of cetyl alcohol, stearyl alcohol, behenyl alcohol and mixtures thereof;
   (c) from about 0.01% to about 5% of an anionic particulate wherein the anionic particulates are either particulates which naturally have anionic charge, wherein the particulate which naturally has anionic charge is a metal carbonate; or non-anionic particulates which are coated or premixed by anionic polymers, wherein the non-anionic particulate which is coated or premixed by an anionic polymer, is metal pyrithione coated or premixed by anionic polymers;
   (d) from about 0.01% to about 5% of a cationic polymer wherein the cationic polymer is polyquaternium-6 having a weight average molecular weight of from about 1,200 g/mol to about 150,000 g/mol and
   (e) an aqueous carrier and wherein the hair care composition is substantially free of anionic surfactants wherein the total level of such anionic surfactants is 1% or less.

2. The composition of claim 1 wherein the cationic surfactant system is selected from: mono-long alkyl quaternized ammonium salt having one long alkyl chain which has from 12 to 30 carbon atoms; a combination of mono-long alkyl quaternized ammonium salt having one long alkyl chain which has from 12 to 30 carbon atoms and di-long alkyl quaternized ammonium salt having two long alkyl chains having 12-30 carbon atoms; mono-long alkyl amidoamine having one long alkyl chain which has from 12 to 30 carbon atoms; and a combination of mono-long alkyl amidoamine and di-long alkyl quaternized ammonium salt having two long alkyl chains having 12-30 carbon atoms.

3. The composition of claim 1 wherein the cationic surfactant system is a combination of a mono-long alkyl quaternized ammonium salt having one long alkyl chain which has from 12 to 30 carbon atoms and a di-long alkyl quaternized ammonium salt having two long alkyl chains having 12-30 carbon atoms.

* * * * *